(12) United States Patent
Chou et al.

(10) Patent No.: US 11,194,385 B2
(45) Date of Patent: Dec. 7, 2021

(54) METHOD AND SYSTEM OF OBTAINING AND TRACKING HUMAN POSTURE

(71) Applicant: Chengdu Siwuge Technology Co., Ltd, Chengdu (CN)

(72) Inventors: Mi Chou, Chengdu (CN); Bin Wu, Chengdu (CN)

(73) Assignee: Chengdu Siwuge Technology Co., Ltd, Chengdu (CN)

( * ) Notice: Subject to any disclaimer, the term of this patent is extended or adjusted under 35 U.S.C. 154(b) by 714 days.

(21) Appl. No.: 16/038,594

(22) Filed: Jul. 18, 2018

(65) Prior Publication Data

US 2019/0171279 A1 Jun. 6, 2019

(30) Foreign Application Priority Data

Dec. 4, 2017 (CN) .......................... 201711258283.X

(51) Int. Cl.
| | |
|---|---|
| *G06F 3/01* | (2006.01) |
| *A61B 5/11* | (2006.01) |
| *H04B 5/02* | (2006.01) |
| *H04Q 9/00* | (2006.01) |
| *H04B 5/00* | (2006.01) |

(52) U.S. Cl.
CPC ............ *G06F 3/011* (2013.01); *A61B 5/1116* (2013.01); *A61B 5/1126* (2013.01); *H04B 5/02* (2013.01); *H04Q 9/00* (2013.01); *H04B 5/0081* (2013.01); *H04Q 2209/40* (2013.01)

(58) Field of Classification Search
CPC .. H04Q 9/00; H04Q 2209/00; H04Q 2209/40; H04Q 2209/80; H04B 5/02; H04B 5/0081; A61B 5/1116; A61B 5/1126; A61B 5/1121; A61B 5/1122; A61B 5/1124; A61B 5/1125; G06F 3/011; G06F 3/017
See application file for complete search history.

(56) References Cited

U.S. PATENT DOCUMENTS

| | | | | |
|---|---|---|---|---|
| 5,224,121 A | * | 6/1993 | Schorman .............. | H04B 1/713 375/135 |
| 5,744,953 A | * | 4/1998 | Hansen ................ | A61B 5/1036 324/207.17 |
| 7,209,790 B2 | * | 4/2007 | Thompson ......... | A61N 1/37254 607/60 |

(Continued)

*Primary Examiner* — Franklin D Balseca
(74) *Attorney, Agent, or Firm* — Rowan P. Smith; Messner Reeves LLP

(57) ABSTRACT

The present invention discloses a method and a system of obtaining and tracking the posture of a subject. Electromagnetic field transceivers may be placed at various locations on the subject, and may be coupled to a processor device, which may be disposed on the back of the subject. The processor device may send waveforms to selected electromagnetic field transceivers located at positions to be tracked. The selected electromagnetic field transceivers may transmit signals corresponding to these waveforms to additional electromagnetic field transceivers located near an origin point. Signals received by these additional electromagnetic field transceivers may be sent to the processor device, which may, based on voltage amplitudes/magnitudes of the received signals, determine the positions and motion trajectories for the electromagnetic field transceivers, which may correspond to positions and motion trajectories of different parts of the subject's body.

19 Claims, 9 Drawing Sheets

(56) References Cited

U.S. PATENT DOCUMENTS

| | | | |
|---|---|---|---|
| 8,888,721 B2* | 11/2014 | Gettelman | A61B 34/10 |
| | | | 600/595 |
| 9,583,836 B2* | 2/2017 | Kato | H01Q 21/065 |
| 10,324,494 B2* | 6/2019 | Camacho Perez | G06F 1/163 |
| 2005/0046608 A1 | 3/2005 | Schantz et al. | |
| 2008/0319349 A1* | 12/2008 | Zilberman | A61B 5/0031 |
| | | | 600/587 |
| 2009/0278791 A1 | 11/2009 | Slycke et al. | |
| 2009/0322763 A1 | 12/2009 | Bang et al. | |
| 2015/0276789 A1* | 10/2015 | Wang | G01P 15/097 |
| | | | 702/141 |
| 2017/0151023 A1 | 6/2017 | Shmarak et al. | |
| 2018/0123843 A1* | 5/2018 | Teichmann | H04L 7/0334 |

* cited by examiner

102

Transmitting, by One or More First Type Electromagnetic Field Radiators Installed on Human Torso, One or More Electromagnetic Signals to a Processor, and Transmitting, by One or More Second Type Electromagnetic Field Radiators Installed on Human Limbs, One or More Electromagnetic Signals to the Processor

104

Measuring Differences of Voltage Amplitudes of Received Signals of the First Type Electromagnetic Field Radiators Relative to an Electromagnetic Field Radiator Disposed at Origin of a Reference Coordinate, and Calculating Coordinate Information of the First Type Electromagnetic Field Radiators Relative to the Origin

106

Acquiring Motion Trajectories of the Second Type Electromagnetic Field Radiators Based on Relations of Distances and Angles Between the Second Type Electromagnetic Field Radiators and First Type Electromagnetic Field Radiators, and Further Acquiring Coordinate Information of the Second Type Electromagnetic Field Radiators Relative to the Origin by Calculating Coordinate Changes Based on the Motion Trajectories

108

Acquiring Real-time Information of the Human Posture Based on Real-time Coordinate Information of the First Type Electromagnetic Field Radiators Relative to the Origin and Real-time Coordinate Information of the Second Type Electromagnetic Field Radiators Relative to the Origin

FIG. 1

METHOD AND SYSTEM OF OBTAINING AND TRACKING HUMAN POSTURE

CROSS-REFERENCE TO RELATED APPLICATION

The present invention claims priority to pending Chinese Application No. 201711258283X, filed Dec. 4, 2017, and incorporated herein by reference.

BACKGROUND

At present, the main conventional methods of tracking human motion include optical methods, acceleration sensor methods, time-domain microwave methods and electromagnetic field methods. A conventional optical methods use visible light or infrared rays to perform image recognition and tracking of beacons disposed at human joints. The results of which this image recognition and tracking may be then used to detect and track human motion. A disadvantage of this optical method is that the beacons can be occluded, resulting in incomplete or inaccurate tracking of human motion. Moreover, the image processing speed of this optical method tends to be slow while the cost is generally high.

A conventional acceleration sensor method obtains the relative position of human joint at which accelerations sensors are placed by calculating the acceleration of human motion detected by these acceleration sensors. A considerable disadvantage of this acceleration sensor method is that position information relative to the previous position may only be obtained with a high processing cost. Another problem with this acceleration sensor method is that timing calibration needs to be performed for the acceleration sensors, which may generally be inconvenient, causing such method to generally be suitable for only industrial applications such as film production.

A conventional time-domain microwave method extracts the positions of beacons disposed at human joints by calculating propagation delays of signals arriving at different receivers. A disadvantage of this time-domain microwave method is that the volume of the antenna is generally so large that the receivers cannot be installed at sufficient positions on the human body. Therefore, this time-domain microwave method generally requires the subject wearing the beacons to be in a specific space having receivers. The accuracy of this method is generally low, and the computational cost of high accuracy positioning is also high. Additionally, this time-domain microwave method is not generally suitable to capture human motion and, in practice, is mainly used in inventory tracking and logistics management.

Conventional electromagnetic field methods generally correspond to one of two different methods of electromagnetic (EM) field analysis. The first EM field analysis method combines a DC magnetic field and an alternating electric field to generate a nutation field. Due to the use of a DC static field, this first EM field analysis method is generally vulnerable to the interference of metal objects in the measurement area. The second EM field analysis method employs a complex transceiver system having three-dimensional orthogonal antenna groups with three frequencies. The three-dimensional orthogonal antenna groups of the transmitting end respectively transmit a signal with one frequency, which is received by the three-dimensional orthogonal antenna groups of the receiving end individually. The positions of the receiving antennas on the three coordinate axes can then be respectively calculated to further calculate the distance and angle between the receiving antennas and the transmitting antennas. Although a transceiver system may generally be resilient to interference, the structure thereof is generally complex and the extraction of calculating parameters is also generally complicated. Also, this transceiver system is generally too expensive to be used for common entertainment. In sum, both the first and second EM field analysis methods include transmitting antennas that are disposed at locations independent of a tracked person, while the receiving antennas are disposed on the body of the tracked person as beacons. Therefore, the tracked person must stay within a certain range of the locations of the transmitting antennas, causing the movement of the tracked person to be limited.

It is within this context that embodiments of the present invention arise.

BRIEF SUMMARY

The present invention provides a method and a system of obtaining a human posture that has the technical effects of convenience, fast response, low cost, and only one calibration.

In an embodiment of the present invention, a method may include receiving, by a first electromagnetic field transceiver disposed on a limb of subject from a processor device, a waveform generated by a transmit waveform generating circuit of the processor device. The method may further include transmitting, via an antenna of the first electromagnetic field transceiver, a signal corresponding to the waveform. The method may further include receiving, via an antenna of a second electromagnetic field transceiver, the signal. The method may further include sending, by the second electromagnetic field transceiver, the received signal to the processor device. The method may further include determining, with the processor device, the voltage of the received signal. The method may further include determining, with the processor device, a coordinate corresponding to a position of the first electromagnetic field transceiver relative to a position of the second electromagnetic field transceiver based at least on the determined voltage.

In some embodiments, the method may further include amplifying, with an amplification circuit of the processor device, the received signal with the amplification circuit, sending, by the amplification circuit, the received signal to a data acquisition card of the processor device, converting, with an analog-to-digital convertor of the data acquisition card, digitizing the received signal, sending, by the digital acquisition card, the received signal to a filtering process block of the processor device, filtering, with the filtering process block, the received signal, and sending, by the filtering process block, the received signal to a signal processing circuit of the processor device, wherein the signal processing circuit performs the steps of determining the voltage of the received signal and determining the coordinate corresponding to the position of the first electromagnetic field transceiver relative to the position of the second electromagnetic field transceiver based at least on the determined voltage.

In some embodiments, determining the coordinate corresponding to the position of the first electromagnetic field transceiver relative to the position of the second electromagnetic field transceiver based at least on the determined voltage may include accessing, with the processor device, a look-up table stored in a memory device coupled to the processor device, and comparing, with the processor device, the determined voltage to the look-up table to determine the coordinate.

In some embodiments, the second electromagnetic field transceiver is disposed on a torso of the subject.

In some embodiments, the antenna is a low frequency antenna that comprises a coil coupled in parallel with a capacitor In some embodiments, the method may further include, with a signal switching matrix of the processor device, selecting the first electromagnetic field transceiver for transmission of the waveform, and with the signal switching matrix of the processor device, selecting the second electromagnetic field transceiver for reception of the waveform.

In some embodiments, the method may further include storing, with the processor device, the coordinate at a memory device coupled to the processor device, generating, with the processor device, a motion trajectory of the first electromagnetic field transceiver over time based on a plurality of coordinates of the first electromagnetic field transceiver stored at the memory device, storing, at the memory device, the generated motion trajectory, sending, from the non-transitory computer-readable memory, the generated motion trajectory to an electronic device, and depicting, as part of a user interface shown on a display of the electronic device, an computer generated model of a human that is animated based at least on the generated motion trajectory.

In an embodiment of the present invention, a system may include a first transceiver disposed on an extremity of a subject and comprising a first antenna, a second transceiver disposed on a torso of the subject and comprising a second antenna, and a processor device coupled to the first and second transceivers via cables. The processor device may include a signal processing circuit, a signal source coupled to the signal processing circuit, the signal source being configured to generate a waveform, and a signal switching matrix coupled to the signal processing circuit, the signal source, the first transceiver, and the second transceiver, the switching matrix being configured to route the waveform to the first transceiver, the first transceiver being configured to transmit a signal corresponding to the waveform via the first antenna, the second transceiver being configured to receive the signal as a first received signal via the second antenna and to send the first received signal to the switching matrix, the switching matrix being configured to route the first received signal to the signal processing circuit, and the signal processing circuit being configured to determine a position of the first transceiver based on a first voltage of the first received signal.

In some embodiments, the system may include a third transceiver disposed on the torso of the subject and comprising a third antenna, the third transceiver being configured to receive the signal as a second received signal via the second antenna and to send the second received signal to the switching matrix, the switching matrix being configured to route the second received signal to the signal processing circuit, and the signal processing circuit being configured to determine the position of the first transceiver based further on a second voltage of the second received signal. The system may further include a memory coupled to the signal processing circuit, the memory being configured to store a look-up table that relates voltages of signals received by the second and third transceivers from the first transceiver to coordinates, the signal processing circuit being configured to compare the first voltage and the second voltage to the look-up table to identify first and second coordinates, the signal processing circuit being configured to identify which of the first and second coordinates has the lowest root-mean square error, the identified coordinate of the first and second coordinates corresponding to the position of the first transceiver, and the memory being configured to store the identified coordinate. The memory may be configured to store a plurality of coordinates corresponding to positions of the first transceiver over time, the signal processing circuit being configured to generate a motion trajectory of the first transceiver based on the plurality of coordinates, and the memory being configured to store the motion trajectory.

In some embodiments, the first transceiver may include a port coupled to a first cable of the cables, the port configured to receive the waveform, a ground terminal, a coil having an inductance and being coupled between the port and the ground terminal, a capacitance coupled in parallel with the coil between the port and the ground terminal, the coil and the capacitance forming the first antenna, and a painted circuit antenna coupled to the port and configured to operate in a 2.4 GHz frequency band.

In some embodiments, the processor device may further include an amplifier configured to amplify the first received signal, a digital acquisition card configured to digitize the first received signal, and a filtering process block configured to perform digital filtering of the first received signal.

In some embodiments, the system may further include a wearable harness that comprises the processor device, the cables, the first transceiver, and the second transceiver.

For making the above and other purposes, features and benefits become more readily apparent to those ordinarily skilled in the art, the preferred embodiments and the detailed descriptions with accompanying drawings will be put forward in the following descriptions.

BRIEF DESCRIPTION OF THE DRAWINGS

The present invention will become more readily apparent to those ordinarily skilled in the art after reviewing the following detailed description and accompanying drawings, in which:

FIG. 1 is an illustrative process flow of a method of tracking a human posture in accordance with an embodiment of the present invention.

DETAILED DESCRIPTION

Figure 2:
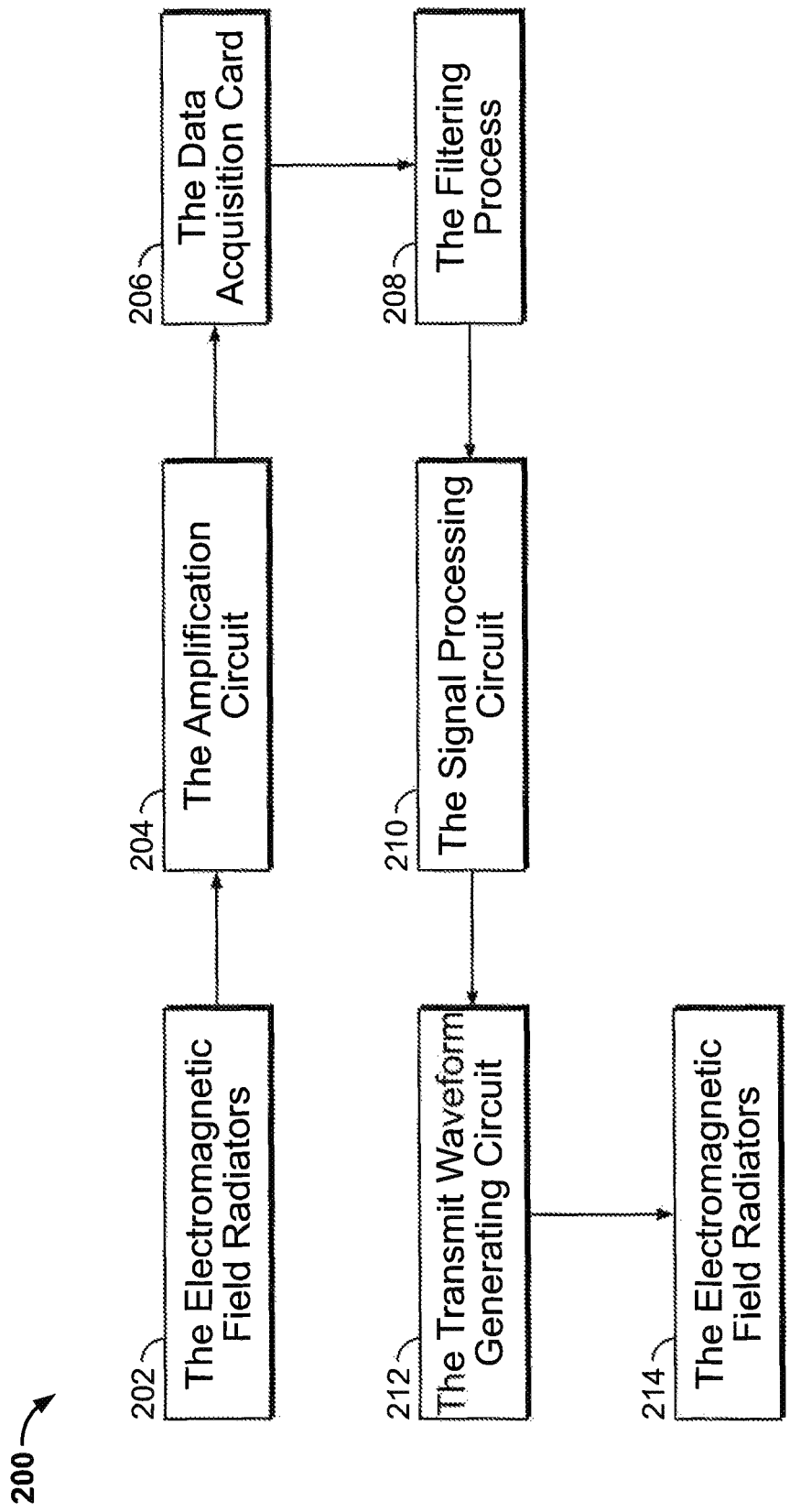
FIG. 2 is a schematic diagram of a hardware composition of a system for tracking a human posture in accordance with an embodiment of the present invention.

The present invention will now be described more specifically with reference to the following embodiments. It should be noted that the following descriptions of preferred embodiments of this invention are presented herein for purpose of illustration and description only. It is not intended to be exhaustive or to be limited to the precise form disclosed.

A first type of electromagnetic field transceivers and a second type of electromagnetic field transceivers may be respectively installed on the human torso and human limbs; selected electromagnetic field transceivers of the first type may transmit signals to selected electromagnetic field transceivers of the second type. The electromagnetic field transceivers receiving the signals transfer the received signals to a processor device; the processor device includes circuitry that measures differences of the voltage amplitudes of the received signals, then calculates coordinate information of the first type of electromagnetic field transceivers relative to an origin point. The processor device may acquire motion trajectories of the second type of electromagnetic field transceivers based on relations of distances and angles between the second type of electromagnetic field transceivers and first type of electromagnetic field transceivers, and may further acquires coordinate information for the second type of electromagnetic field transceivers relative to the origin by calculating coordinate changes (e.g., changes from a known initial coordinate location) based on the motion trajectories. The processor may obtain real-time information of a human posture based on real-time coordinate information of the first type of electromagnetic field transceivers relative to the origin and real-time coordinate information of the second type of electromagnetic field transceivers relative to the origin.

The electromagnetic field transceivers may be used to transmit and receive signals. For instance, the electromagnetic field transceivers disposed at the positions to be measured (e.g., at extremities of a subject) radiate the signals generated by a transmit waveform generating circuit of the processor device to the surroundings to form a local field distribution. Then the electromagnetic field transceivers disposed at the positions for measuring (e.g., at the torso of a subject) receive the signals. After being amplified by an amplification circuit, the signals may be collected by a data acquisition card and converted from analog signals to digital signals. After digital filtration, the digital signals may be transferred into a signal processing circuit to perform a computing process.

Generally, the origin point used as a reference may be a certain point on the tracked subject's back which can be manually set according to actual needs. The change of the posture of the subject may be obtained based on the coordinate changes of the first type of electromagnetic field transceivers relative to the origin and the coordinate changes of the second type of electromagnetic field transceivers relative to the origin.

The electromagnetic field transceivers and the processor may be installed directly or indirectly on a human body, and connections between the processor device and the electromagnetic field transceivers may be wired or wireless.

After measuring the differences of the voltage amplitudes of the received signals of the first type of electromagnetic field transceivers (e.g., relative to the electromagnetic field transceiver disposed at the origin of the reference coordinate), coordinate information of the first type of electromagnetic field transceivers relative to the origin may be calculated based on a corresponding relationship between the voltage amplitude and coordinate information.

One or more technical schemes provided in the present invention have at least the following technical effects or benefits. As all of the electromagnetic field transceivers are disposed on the tracked subject's body and no external device is needed to perform tracking, thus embodiments of the present invention realize posture/motion tracking independent of the environment, which may be advantageous for scenarios in which the motion of a subject must be tracked over a large area that is not conducive to needing external motion tracking hardware. Additionally, embodiments of the present invention may track the absolute coordinates of the position and speed of a subject, avoiding error accumulation, and further avoiding the need for complex timing calibration processes. Furthermore, compared with optical methods of motion tracking and methods that rely on mechanical structures such as an accelerometers and a compass, the measurement of electromagnetic fields adopted by the present invention avoids the comparably longer optical image processing time and mechanical response time associated with such conventional methods, resulting in fast processing speed. Meanwhile, embodiments of the system described herein may provide the technical advantages of simple configuration, low-cost hardware and the need for only one calibration.

As shown in FIG. 1 and FIG. 2, the present invention provides a method of obtaining and tracking the posture (e.g., position and motion of a body) of a person (e.g., a subject). At step 102 of FIG. 1, one or more of a first type of electromagnetic field radiators (e.g., transceivers) installed on a human torso may transmit one or more electromagnetic signals to a processor device, and one or more of a second type of electromagnetic field radiators (e.g., transceivers) installed on human limbs (e.g., extremities such as arms, legs, hands, feet, etc.) may transmit one or more electromagnetic signals to the processor device.

At step 104, the processor device may measure differences of voltage amplitudes of received signals of the first type of electromagnetic field radiators relative to an electromagnetic field radiator disposed at an origin reference point, and may calculate coordinate information of the first type of electromagnetic field radiators relative to the origin.

At step 106, the processor device may acquire motion trajectories of the second type of electromagnetic field radiators based on relations of distances and angles between the second type of electromagnetic field radiators and the first type of electromagnetic field radiators, and may further acquire coordinate information of the second type of electromagnetic field radiators relative to the origin by calculating coordinate changes based on the motion trajectories.

At step 108, the processor device may acquire real-time information of the human posture based on real-time coordinate information of the human posture based on real-time coordinate information of the first type electromagnetic field radiators relative to the origin and real-time coordinate information of the second type of electromagnetic field radiators relative to the origin.

A plurality of a first type of electromagnetic field transceivers may be installed on the torso of the subject. For example, the electromagnetic field transceivers may be attached to the torso of the subject using adhesive or may be integrated into a wearable harness (e.g., harness 804 of FIG. 8) worn by the subject. A plurality of a second type of electromagnetic field transceivers may be installed on the limbs and, optionally, the torso of the subject. In some embodiments, the first type of electromagnetic field transceivers may instead be limited to electromagnetic field receivers that only perform signal receive operations, and the second type of electromagnetic field transceivers may instead be limited to electromagnetic field transmitters that only perform signal transmit operations.

A processor device may be electrically, communicatively coupled to the first and second types of electromagnetic field transceivers (e.g., via one or more cables). All of the first type of electromagnetic field transceivers and the second type of electromagnetic field transceivers transmit a plurality of electromagnetic signals to the processor device (e.g., via the one or more cables). The processor device may determine differences between voltage amplitudes of first signals received from the first type of electromagnetic field transceivers relative to an origin signal an electromagnetic field transceiver (sometimes referred to herein as an "origin transceiver") disposed at an origin point corresponding to a reference coordinate. The processor device may then calculate coordinate information corresponding to each of the first type of electromagnetic field transceivers relative to origin point. The processor device may determine motion trajectories of the second type of electromagnetic field transceivers based on relations of distances and angles between the second type of electromagnetic field transceivers and first type of electromagnetic field transceivers. The processor device may then determine coordinate information corresponding to each of the second type of electromagnetic field transceivers relative to the origin point by calculating coordinate changes based on the determined motion trajectories. The processor device may determine real-time information corresponding to the posture of the subject based on real-time coordinate information determined by the processor device for the first type of electromagnetic field transceivers relative to the origin point and further based on real-time coordinate information determined by the processor device for the second type of electromagnetic field transceivers relative to the origin point.

The electromagnetic field transceivers described herein may include first type of electromagnetic field transceivers and a second type of electromagnetic field transceivers, wherein each of the electromagnetic field transceivers comprises an access port for signal access (e.g., in communication with the processor device via a cable), a capacitance connected between the access port and ground, a coil (e.g., which may operate as an antenna, such as a near-field communications (NFC) antenna) connected in parallel with the capacitance, and an oscillator (e.g., a crystal oscillator) connected to the access port. The access port may be connected to a cable, allowing signals to feed from the electromagnetic field transceiver to the cable to the processor device during receiver operations and allowing signals to feed from the processor device to the cable to the electromagnetic field transceiver during transmitter operations. Thus electromagnetic energy can feed to the coil and the oscillator via the capacitance. Low frequency signals may primarily radiate from the coil to form a first near field distribution, while high frequency signals may primarily radiate from the oscillator to form a second near field distribution. The electromagnetic field transceivers convert received signals (e.g., guided electromagnetic waves) transmitted to the electromagnetic field transceivers by the cable into a near quasi-stationary electromagnetic field distribution, and enable the low frequency signals and the high frequency signals to feed simultaneously, realizing two frequency spectrum radiation components with large frequency difference. During receive operations, the coil and the oscillator can convert the surrounding quasi-stationary electromagnetic field into the induced current, which flows to the cable to form the receiving signal, and may be transferred to the processor device via the cable. The aforementioned circuit configuration is not only relatively simple (e.g., requiring relatively few components) and small, but also provides enough of a radiation area (e.g., for the near-quasi-stationary electromagnetic field distribution) to obtain a sufficient radiation distance which is up to 1 meter, filling the technical blanks of the wireless charging coil.

Figure 3:
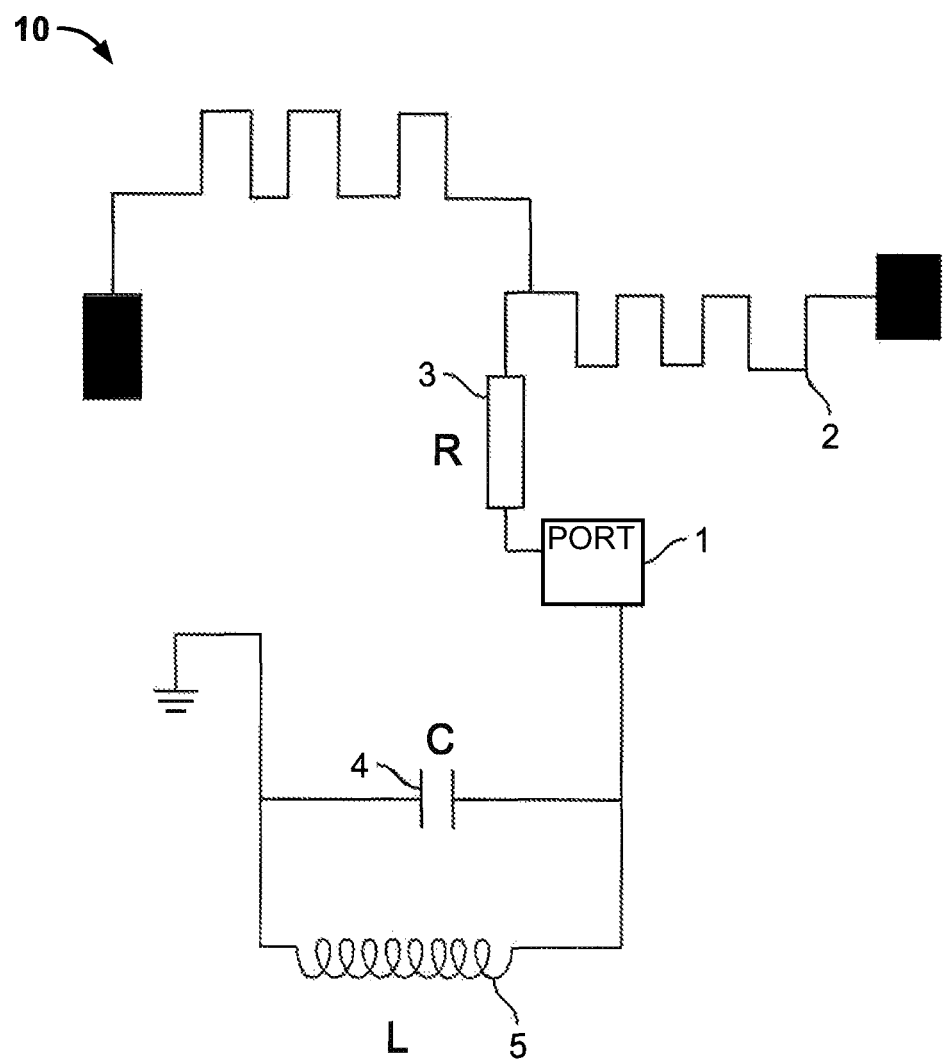
FIG. 3 is a schematic diagram of a structure of an illustrative electromagnetic field transceivers in accordance with an embodiment of the present invention.

An illustrative embodiment of an electromagnetic field transceiver that may, for example, be used in connection with at least the embodiments of FIGS. 1, 2, 4, 5, 8A, and 8B is shown in FIG. 3. As shown, the electromagnetic field transceiver 10 comprises an access port 1, a resistor 3 having a resistance R, a capacitive component 4 having a capacitance C, a coil 5 having an inductance L and an oscillator 2 wherein the access port 1 is connected to the cable for signal access. The capacitance C is connected between the access port 1 and ground (e.g., a terminal that is at a ground voltage or a common voltage). The coil 5 is connected in parallel with the capacitance C. The coil 5 and the capacitance C may, in combination, operate as a low frequency antenna. The oscillator 2 is connected to the access port 1. The oscillator 2 may, for example, be a circuit painted antenna that operates in the Wi-Fi frequency range (e.g., 2.4 GHz), and may be used for calibration of the system. When signals are received by the electromagnetic field transceiver through the cable, low frequency signals and high frequency signals respectively radiate from the coil 5 and the oscillator 2 to form the near field distribution. The electromagnetic field transceiver 10 can further include a separate port (not shown) for realizing the connection between the capacitance C and the ground. For example, such a port may be connected to an electrically grounded housing.

An illustrative hardware composition of a system 200 is shown in FIG. 2. The electromagnetic field radiators (sometimes referred to herein as transceivers) 202 and 214 are disposed throughout the body of the tracked person and connected to the processor device via the cable. The electromagnetic field transceivers 202 and 214 are used to transmit and receive signals. For instance, the electromagnetic field transceivers 214 disposed at predefined positions to be measured radiate signals (e.g., transmit waveforms) generated by a transmit waveform generating circuit 212 to the surroundings to form a near field distribution. Then the electromagnetic field transceivers 202 (e.g., electromagnetic field transceivers of the first type disposed at the positions for measuring) receive the signals may measure the near field distribution (e.g., produced, at each electromagnetic field transceivers 214, by the coil 5 of FIG. 3). Time division multiplexing (TDM) may be used in combination with one or more switching matrices (e.g., signal switching matrix 412 of FIG. 4) in order to route signals from the transmit waveform generating circuit 212 to the electromagnetic field transceivers 214, and to route signals from the electromagnetic field transceivers 202 to the elements 204-210. A detailed example of TDM operations that may be performed by the system is provided below in connection with FIG. 4.

After being amplified by an amplification circuit 204, the measured signals are collected by a data acquisition card 206 and converted from analog signals to digital signals (e.g., by an analog-to-digital converter (ADC) circuit that may be included in the data acquisition card 206). A filtering process block 208 may perform digital filtration on the digital signals output by the data acquisition card. After digital filtration, the digital signals are transferred into a signal processing circuit 210, which may perform an arithmetic processing calculation based on the filtered digital signals output by the filtering process block 208.

The amplification circuit 204 may use a hybrid integrated circuit, which may be, for example, established by simulating the BJT triode. The data acquisition card 206 may use an ADC chip with low cost and high-precision. In some embodiments, the filtering process block 208 may be enabled by employing digital filter software executed by the processor (e.g., processor 410 of FIG. 4) to perform digital filtering operations. In other embodiments, the filtering process block 208 may be a signal filtering circuit including one or more discreet components such as capacitors, resistors, and inductors. The signal processing circuit 210 may, for example, include a low-cost FPGA circuit, ASIC circuit, or ARM circuit. The transmit waveform sent to the electromagnetic field transceiver(s) 214 may be generated by the transmit waveform generating circuit 212 (e.g., using a peripheral operational amplifier and a crystal oscillator circuit) according to instructions received from the signal processing circuit 210. It should be noted that components 204-212 may all be part of a centralized processor device (e.g., processor device 410 and 808 of FIGS. 4 and 8B)

The electromagnetic field transceivers 202 and 214 may be, for example, disposed on the tracked person's garment or a belt binding device. The processor device is connected with each of the electromagnetic field transceivers 202 and 214 through the cable and may calculate the amplitudes and the phases of the signals received by at least a subset of the electromagnetic field transceivers, and may further calculate the distance and angle between any two of the electromagnetic field transceivers 202 and 214. After distances and angles between multiple pairs of the electromagnetic field transceivers 202 and 214 are determined by the processor device, the posture of the human body can be also determined by the processor device.

The algorithm for calculating the relative positions of two of the electromagnetic field transceivers 202 and 214 will now be described.

Most of the electromagnetic field transceivers disposed on the back or the chest of the torso of the subject may be the first type of electromagnetic field transceivers. The first type of electromagnetic field transceivers may use the central area of the back as the origin point of the reference coordinate. When the body of the subject is in a natural upright state, the initial position of each of the first type of electromagnetic field transceivers is known (e.g., stored in a look-up table (LUT) of a non-transitory computer-readable memory device coupled to the processor device, such as the memory device 418 of FIG. 4). In the process of movement of the subject, the relative positions of the first type of electromagnetic field transceivers generally change in a one-dimensional direction due to the limited movement range of the human torso. Consequently, with the measurement of the differences of the voltage amplitudes of the signals received from the first type of electromagnetic field transceivers (e.g., received by a receiving electromagnetic field transceiver) relative to the voltage amplitude of a signal received from one of the first type of electromagnetic field transceivers (e.g., received by the receiving electromagnetic field transceiver) that is disposed at the origin point of the reference coordinate, the change in the positions of the measured first type of electromagnetic field transceivers relative to the origin can be calculated directly by the processor device.

The remaining electromagnetic field transceivers disposed on the human torso and the electromagnetic field transceivers disposed on the human limbs may be the second type of electromagnetic field transceivers. The motion trajectories of the second type of electromagnetic field transceivers may be determined according to the relations of distances and angles between the second type of electromagnetic field transceivers and first type of electromagnetic field transceivers Subsequently, the coordinate information of the second type of electromagnetic field transceivers relative to the origin can be acquired by calculating coordinate changes, as initial coordinates for the second type of electromagnetic field transceivers will now be known.

The calculating method for the relative positions of the second type of electromagnetic field transceivers and the first type of electromagnetic field transceivers will now be described.

According to the calculation formula for the electromagnetic field induced voltage:

$$dB = k \frac{Id1 \times a_R}{R^2}$$

In the aforementioned calculation formula, dB refers not to decibels, but instead to a magnetic flux density segment in Tesla, wherein one Tesla equals one Weber per square meter (Wb/m$^2$); dl refers to a current segment (e.g., a portion of a wire/path through which current is travelling) in a current direction (e.g., the direction in which the current is travelling); $a_R$ refers to a unit vector from dl to a point P; R refers to a distance from the current segment dl to point P; I refers to the electrical current; and K is the proportionality constant.

According to the Biot-Savart law of the space magnetic field formula, the magnetic flux density of any current segment formed at a certain point in space is inversely proportional to square of the distance between the certain point and the current segment, and proportional to the cross product of the included angle between the certain point and the direction of the current segment.

When a signal is transmitted by one of the electromagnetic field transceivers (referred to here as the transmitting electromagnetic field transceiver) and received by another one of the electromagnetic field transceivers (referred to here as the receiving electromagnetic field transceiver), according to the integral form of Faraday's law in Maxwell equation, with the same frequency, the signal strength (i.e. voltage amplitude) received by the receiving electromagnetic field transceiver is determined by the magnetic flux density of coil of the receiving electromagnetic field transceiver generated by the transmitting electromagnetic field transceiver. The signal strength is linear with the magnetic flux density. On the other hand, the shape of the antenna and the turns of the coil are constant so that their contributions to the total magnetic flux density of the coil obtained by integrating according to the Biot-Savart law are also constant. Therefore, the magnetic flux density is only determined by the distance and the angle between the receiving electromagnetic field transceiver and the transmitting electromagnetic field transceiver.

Figure 4:
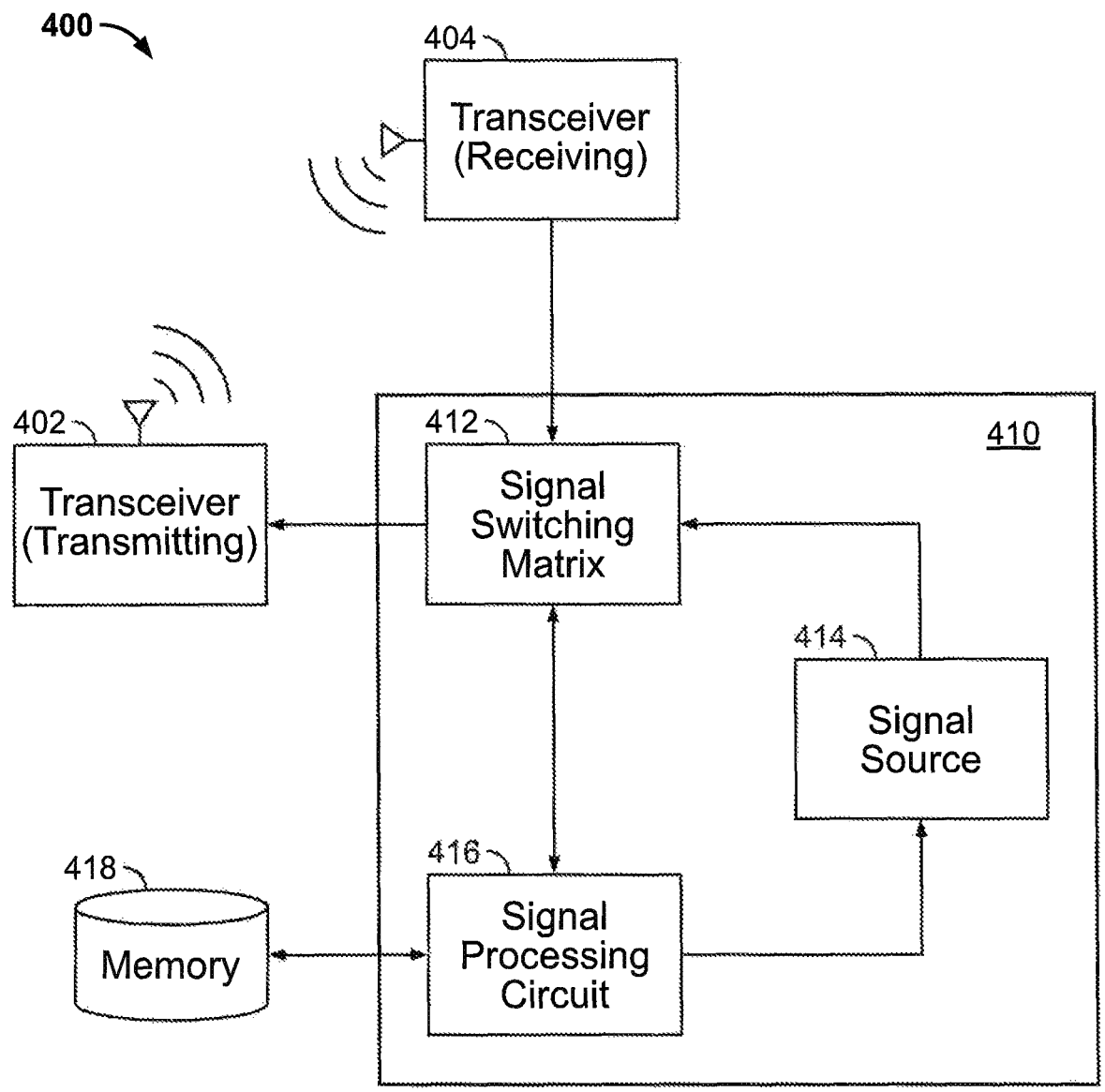
FIG. 4 is a schematic diagram of an illustrative system that may track human posture in accordance with an embodiment of the present invention.

FIG. 4 shows an illustrative system 400 that may track the posture and movement of a body (e.g., a human body. Electromagnetic field transceivers 402 and 404 may be placed at defined locations on a human body (e.g., as described previously in connection with electromagnetic field transceivers 202 and 214). Electromagnetic field transceivers 402 and 404 may be coupled to a processor device 410, which may include a signal switching matrix 412, a signal source 414, a signal processing circuit 416, and a non-transitory computer-readable memory device 418. Particularly, the transmitting electromagnetic field transceiver 402 and the receiving electromagnetic field transceiver 404 may be coupled to the signal switching matrix 412 (e.g., via physical cables).

For example, the signal switching matrix 412 may include two different switching matrices: a receive-switching matrix and a transmit-switching matrix. Signals provided to the transmitting electromagnetic field transceiver 402 may be routed through the transmit-switching matrix, while signals received by the processor 410 from the receiving electromagnetic field transceiver 404 may be routed through the receive-switching matrix. It should be understood that transmitting electromagnetic field transceiver 402 may be part of a larger group of transmitting electromagnetic field transceivers, and that receiving electromagnetic field transceiver 404 may be part of a larger group of receiving electromagnetic field receivers. Thus, TDM may be applied by the signal switching matrix 412 to uniquely identify a given transmitting electromagnetic field transceiver to send a signal generated by the signal source 414 to, and may further by applied by the signal switching matrix 412 to uniquely identify a given receiving electromagnetic field transceiver to receive a signal from. In this way, For example, from time t1 to time t2 (e.g., corresponding to a period of 100 microseconds), the signal switching matrix 412 may route signals to be transmitted to a first transmitting electromagnetic field transceiver and may route signals produced by a first receiving electromagnetic field transceiver to the signal processing circuit 416. In this way, the position of the first transmitting electromagnetic field transceiver may be determined with respect to the position of the first receiving electromagnetic field transceiver. From time t2 to t3 (e.g., corresponding to a period of 100 microseconds), the signal switching matrix 412 may route signals to be transmitted to a second transmitting electromagnetic field transceiver and may route signals produced by a second receiving electromagnetic field transceiver to the signal processing circuit 416. In this way, the position of the second transmitting electromagnetic field transceiver may be determined with respect to the position of the second receiving electromagnetic field transceiver. By only routing signals to one selected transmitting electromagnetic field transceiver and from one selected receiving electromagnetic field transceiver per time period, control of and data collection from individually selected pairs of electromagnetic field transceivers is enabled.

The signal processing circuit 416 may instruct the signal source 414 to generate signals having defined frequencies and amplitudes. Signals generated by the signal source 414 may be output to the signal switching matrix 412, which may be configured to route the signals to one or more selected, transmitting electromagnetic field transceivers, including transceiver 402. Transmitting electromagnetic field transceiver 402 may amplify and transmit the signals received from the signal switching matrix, and may contribute to a near field distribution formed from signals transmitted by multiple transmitting electromagnetic field transceivers.

Receiving electromagnetic field transceiver 404 may receive the signal wirelessly transmitted by the transmitting electromagnetic field transceiver 402, and may amplify, digitize, and/or filter this signal, before sending the modified signal to the signal processing circuit 416 through the signal switching matrix 412. The signal processing circuit 416 may then process the signals received from the receiving electromagnetic field transceiver 404 in order to determine the position and motion trajectory of the transmitting electromagnetic field transceiver 402. For example, multiple position determinations may be made for the transmitting electromagnetic field transceiver 402 periodically over time in order to determine the motion trajectory of the transmitting electromagnetic field transceiver 402. The motion trajectory may be stored in the memory 418 along with motion trajectories for multiple other electromagnetic field transceivers attached to the subject. In some embodiments, the generated motion trajectory may be displayed as part of a user interface of an electronic device (e.g., as part of a user interface shown on a display of a desktop or laptop computer or of a smartphone or tablet device) coupled to the memory 418 or to the processor device 410. For example, a computer generated model of a human may be depicted by the user interface, and the computer generated model may move in an animated fashion according to the motion trajectories generated for multiple electromagnetic field transceivers based on the coordinates stored at the memory 418 (e.g., that may be sent to the electronic device from the memory 418).

In this way, the generated motion trajectories may be visualized in real-time (e.g., accounting for realistic delays associated with data transmission and processing) or at a later point in time. While only two electromagnetic field transceivers are shown here, it should be understood that additional receiving and transmitting electromagnetic field transceivers may be coupled to the signal switching matrix and may send and receive signals to and from the signal processing circuit 416. The memory device 418 may be communicatively coupled (e.g., via a wired or wireless connection) to the signal processing circuit 416 of the processor device 410. In some embodiments, the memory device 418 may instead be included as part of the processor device 410 and may be, for example, coupled to the signal processing circuit 416 via interconnects on a circuit board on which the signal processing circuit 416 is disposed. The signal processing circuit 416 may compare voltages of signals received from the receiving electromagnetic field transceiver 404 to one or more look-up tables (LUTs) stored in the memory 418. Position coordinate data for the transmitting electromagnetic field transceiver may be collected and stored in the memory 418 over time, as it is periodically determined by the signal processing circuit 416.

Figure 5:
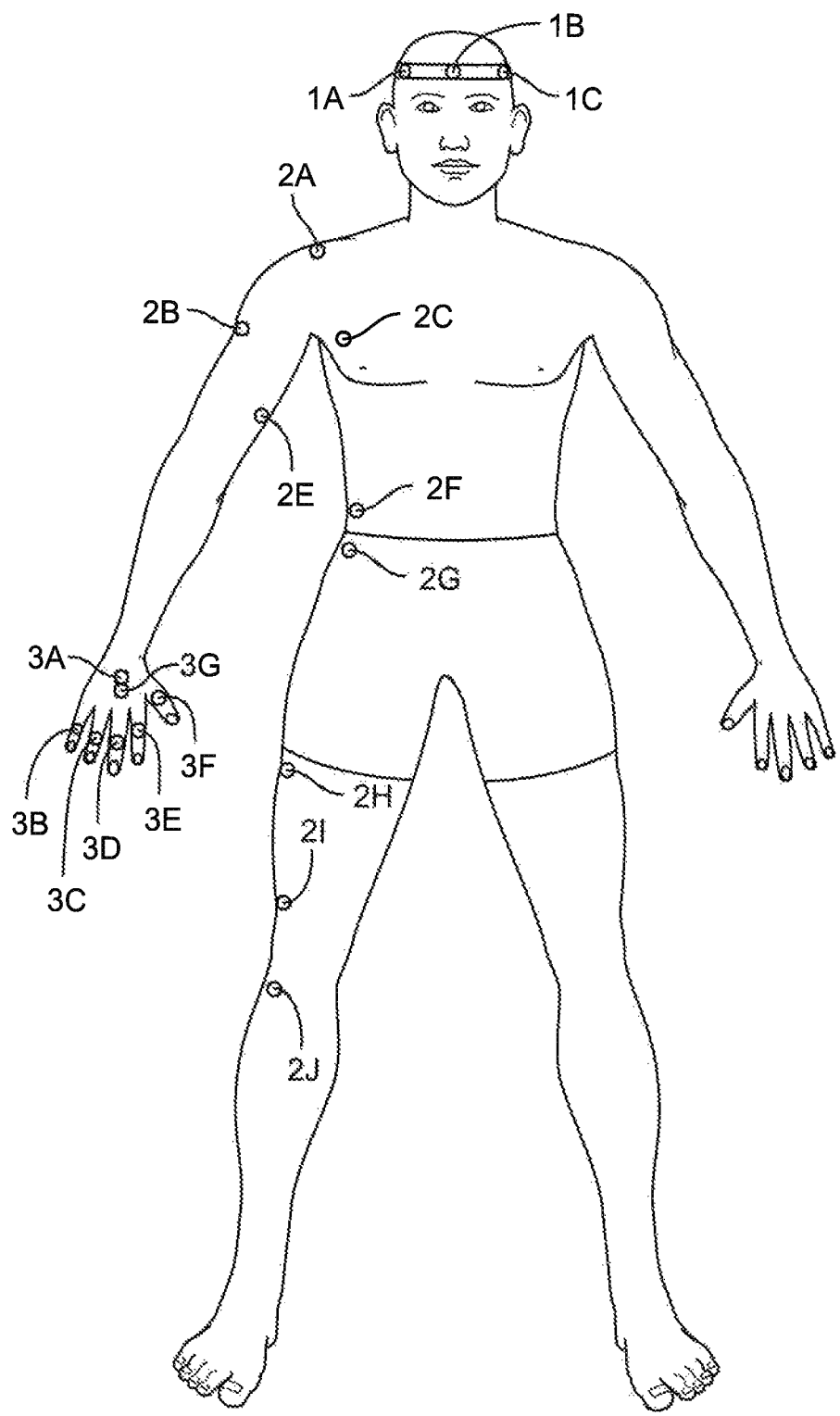
FIG. 5 is a diagram showing an illustrative placement of transceivers on a human body in accordance with an embodiment of the present invention.

An example of how posture and movement of a subject may be obtained (e.g., by the system 400 of FIG. 4) will now be described in the context of the illustrative electromagnetic field transceiver placement 500 shown in FIG. 5. As shown, the serial number of one of the second type of electromagnetic field transceivers disposed on the thigh of the subject is 2H. When being tracked, 2H transmits signals are received by two of the first type of electromagnetic field transceivers, 2G and 2F.

The movement range of 2H relative to 2G and 2F is limited by the human joints and muscle actions. In relation to 2G, 2H is only able to move within a distance of 4-8 cm (depending on raising the thigh and lateral valgus motion) and an angle of 0-130°. Similarly, in relation to 2F, 2H is only able to move within a distance of 6-10 cm (depending on raising the thigh and lateral valgus motion) and an angle of 0-130°.

Thus, within the movement range described above, when 2G and 2F receive the signals transmitted from 2H, the measured signal strength Vout2g and Vout2f also correspond to the distance r relation and the included angle θ relation of 2H and 2G. The relations are as follows:

$Vout2g = f(r1, \theta1);$ $4 < r1 < 8;$ $0 < \theta1 < 130;$ $Vout2f = f(r2, \theta2)$ $6 < r2 < 10;$ $0 < \theta2 < 130;$ wherein r1 refers to a distance between 2G and 2H; θ1 refers to an angle between 2G and 2H; r2 refers to a distance between 2F and 2H; and θ2 refers to an angle between 2F and 2H. The calculation formula for f(r, θ) is as follows:

$$f(r, \theta) = \frac{A \cdot \mu N_1 N_2}{4\pi} \oint_{c_1} \oint_{c_2} \frac{\cos \theta dl_1 dl_2}{r};$$

In the above formula, A refers to the voltage transfer coefficient that is a constant related to the circuit configuration of each of the electromagnetic field transceivers; μ refers to the air permeability; N2 refers to the number of turns of the coil of the transmitting electromagnetic field radiator; N1 refers to the number of turns of the coil of the receiving electromagnetic field radiator; C1 refer to the integration along the transmitting coil loop; C2 refer to the integration along the receiving coil loop; θ refers to the included angle between the transmitting coil and the receiving coil; r refers to the distance between the transmitting current segment and the receiving current segment; and $dl_1$ and $dl_2$ are integration units.

In view of the above formula, the voltage amplitudes of the receiving electromagnetic field transceiver disposed at the known position and angle can be calculated. A LUT may be stored in a memory device (e.g., memory device 418 coupled to the processor device 410), which may include a position/angle-voltage matrix, such as the one shown in Table 1, below.

TABLE 1

| Angle θ1 (°) | Angle θ2 | Transceiver 2F (Voltage - normalized) | Transceiver 2G (Voltage - normalized) |
|---|---|---|---|
| 0 | 0 | 3073 | 8268 |
| 15 | 90 | 3729 | 11287 |
| 15 | 60 | 3475 | 11288 |
| 15 | 45 | 3255 | 10827 |
| 15 | 30 | 3263 | 10330 |
| 15 | 15 | 3062 | 10504 |
| 15 | 0 | 2833 | 8621 |
| 15 | −15 | 2723 | 8572 |

With (i) the measured voltage amplitudes of the signals received by the receiving electromagnetic field transceivers (2G and 2F), (ii) the measured values of Vout2g and Vout2f, (iii) the constraints of r and θ, and (iv) the position/angle-voltage matrix calculated according to the aforementioned formula, the position/angle point of the matrix that has a lowest root mean square error with the voltage output by the receiving electromagnetic field transceivers (G2 and F2) is calculated by Newton optimization method of minimum criterion of root mean square error (various similar maturation algorithms for solving such problem are known, such as Runge-Kutta method). It should be understood that interpolation may be used when determining the values for θ1 and θ2 based on the LUT, as the defined relationships between the normalized voltage at transceiver 2G and the normalized voltage at transceiver 2F versus θ1 and θ2 may not be exhaustive (e.g., there may be gaps in the data stored in the LUT that may require interpolation to fill). Finally, the corresponding parameters of θ1 and θ2 of 2H are determined according to the LUT. After coordinate conversion, the real-time coordinate of 2H relative to the origin is acquired. In order to track motion trajectory of 2H, the real-time coordinate of 2H may be periodically determined according to the above process and multiple real-time coordinate values collected over time may be stored in a memory device (e.g., memory device 418 of FIG. 4) coupled to the processor device. In some embodiments, WiFi antennas (e.g., oscillator 2 of FIG. 3) in electromagnetic field transceivers 2G and 2F may be used to detect phase variation to improve the accuracy of the determination of the real-time coordinates of 2H.

The amount of the receiving electromagnetic field transceivers for tracking one of the electromagnetic field transceivers can be increased when the computational efficiency is poor.

The positioning method for determining positions of the other electromagnetic field transceivers is similar to the method described above. During the calculation of the position of the other electromagnetic field transceivers, the constraints of r and θ are determined by the movement range of human joints where the electromagnetic field transceivers are located. Such movement range can be obtained via the exercise physiological analysis and may, for example, be stored in the memory device (e.g., memory device 418 of FIG. 4) coupled to the processor device. The global absolute coordinate of the mark points of the human motion (e.g., the positions of the electromagnetic field transceivers) relative to a certain fixed point (e.g., the origin) disposed on the back of the subject can be obtained by the processor device with the determination of relative positional relationships of all of the electromagnetic field transceivers. When in use, the tracked subject starts performs a standard motion which is used by the system to complete a calibration process. Later, the tracked subject can move freely without additional calibration processes.

Figure 6:
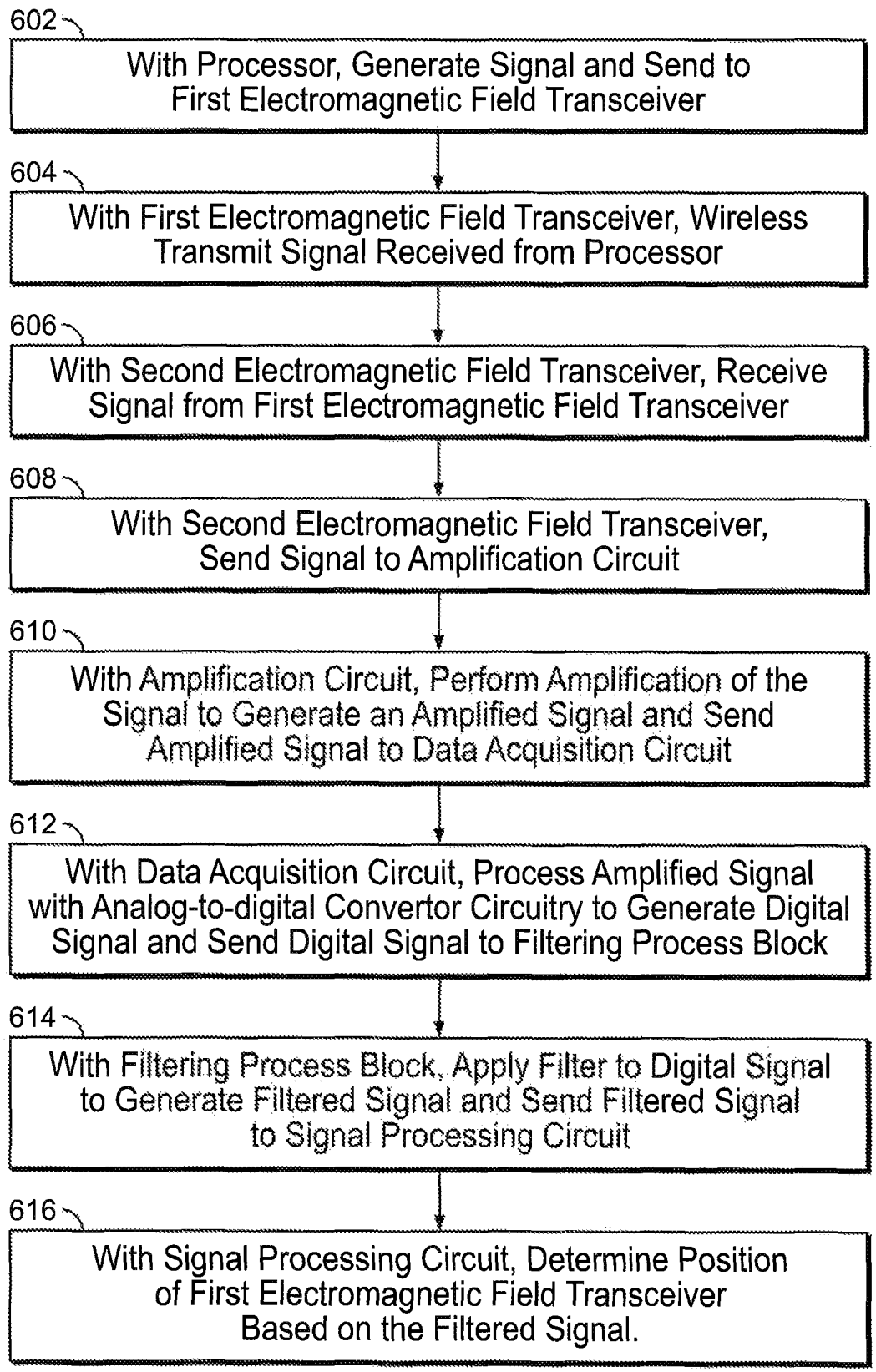
FIG. 6 is an illustrative process flow for a method by which the position of an electromagnetic field transceiver may be determined in accordance with an embodiment of the present invention.

FIG. 6 shows an illustrative process flow for a method of obtaining and tracking the posture and movement of a body. The method may, for example, be performed by the system 200 of FIG. 2 or the system 400 of FIG. 4.

At step 602, a processor device (e.g., the transmit waveform generating circuit 212 of FIG. 2; the processor device 410 of FIG. 4) may generate a signal (e.g., a waveform) and may send the generated signal to a first electromagnetic field transceiver (e.g., one of electromagnetic field transceivers 214 of FIG. 2; electromagnetic field transceiver 402 of FIG. 4). For example, signal may be transmitted from the processor device to the first electromagnetic field generator via a physical cable and, in some embodiments, through a switching matrix (e.g., switching matrix 412 of FIG. 4).

At step 604, the first electromagnetic field transceiver may wirelessly transmit the signal received from the processor device. For example, the signal may be wirelessly transmitted in a predefined band, such as the 2.4 GHz band.

At step 606, a second electromagnetic field transceiver (e.g., one of electromagnetic field transceivers 202 of FIG. 2; electromagnetic field transceiver 404 of FIG. 4) may receive the signal wirelessly transmitted by the first electromagnetic field transceiver. The second electromagnetic field transceiver may be located at a defined origin point.

At step 608, the second electromagnetic field transceiver may send the signal to an amplification circuit (e.g., the amplification circuit 204 of FIG. 2) of the processor device (e.g., via a physical cable).

At step 610, the amplification circuit may amplify the signal to generate an amplified signal and may then send the amplified signal to a data acquisition circuit (e.g., data acquisition card 206 of FIG. 2) of the processor device.

At step 612, the data acquisition circuit may digitize the amplified signal (e.g., using analog-to-digital convertor (ADC) circuitry) to generate a digital signal, and may then send the digital signal to a filtering process block (e.g., filtering process block 208 of FIG. 2).

At step 614, the filtering process block may apply one or more filters (e.g., one or more high pass, low pass, band pass, and/or notch filters) to the digital signal to generate a filtered signal and may send the filtered signal to a signal processing circuit (e.g., signal processing circuit 210 of FIG. 2; signal processing circuit 416 of FIG. 4).

At step 616, the signal processing circuit may determine a position of the first electromagnetic field transceiver (e.g., relative to a defined origin point) based on the filtered signal. For example, a LUT stored in a memory device (e.g., memory device 418 of FIG. 4) may be accessed by the processor device, and the magnitude of the voltage of the filtered signal may be compared to the LUT to determine a coordinate corresponding to the position of the first electromagnetic field transceiver relative to the origin point. The determined coordinate may, in some embodiments, be stored the memory device coupled to the processor device, which may enable a motion trajectory to be derived from multiple stored, determined coordinates (e.g., positions) of the first electromagnetic field transceiver collected over time.

It should be understood that the method of FIG. 6 may be performed periodically in order to collect and store multiple determined coordinates of the first electromagnetic field transceiver over time so that a motion trajectory may be calculated for the first electromagnetic field transceiver.

Figure 7:
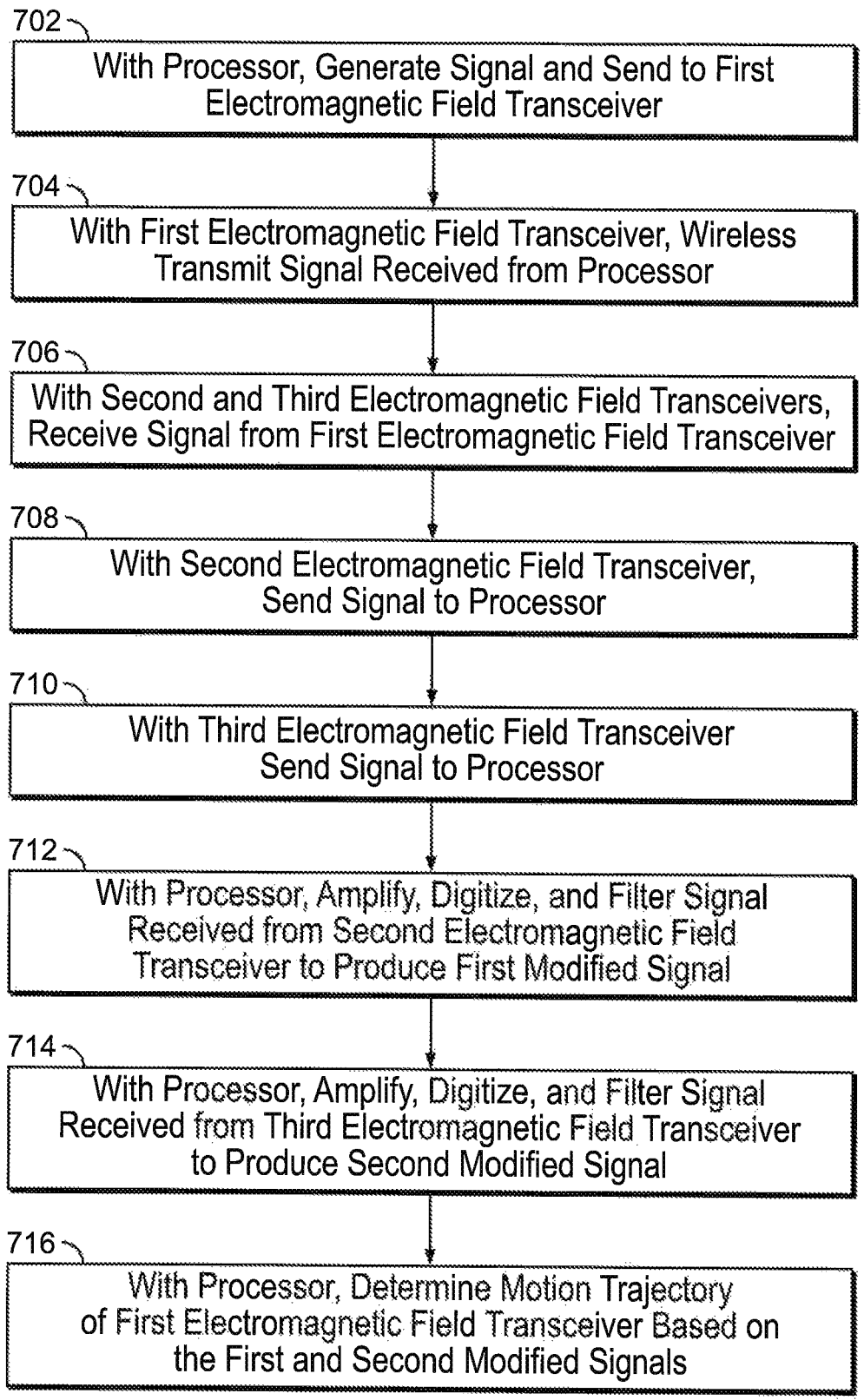
FIG. 7 is an illustrative process flow for a method by which the position and motion trajectory of an electromagnetic field transceiver may be determined in accordance with an embodiment of the present invention.

FIG. 7 shows an illustrative process flow for a method of obtaining and tracking the posture and movement of a body. The method may, for example, be performed by the system 200 of FIG. 2 or the system 400 of FIG. 4.

At step 702, a processor device (e.g., the transmit waveform generating circuit 212 of FIG. 2; the processor device 410 of FIG. 4) may generate a signal (e.g., a waveform) and may send the generated signal to a first electromagnetic field transceiver (e.g., one of electromagnetic field transceivers 214 of FIG. 2; electromagnetic field transceiver 402 of FIG. 4). For example, signal may be transmitted from the processor device to the first electromagnetic field generator via a physical cable and, in some embodiments, through a switching matrix (e.g., switching matrix 412 of FIG. 4).

At step 704, the first electromagnetic field transceiver may wirelessly transmit the signal received from the processor device. For example, the signal may be wirelessly transmitted in a predefined band, such as the 2.4 GHz band.

At step 706, second and third electromagnetic field transceivers (e.g., two of electromagnetic field transceivers 202 of FIG. 2) may receive the signal wirelessly transmitted by the first electromagnetic field transceiver.

At step 708, the second electromagnetic field transceiver may send the signal to the processor device.

At step 710, the third electromagnetic field transceiver may send the signal to the processor device. It should be noted that the signal received by the second electromagnetic field transceiver and the signal received by the third electromagnetic field transceiver will likely have different magnitudes and/or phases.

At step 712, the processor device may amplify, digitize, and filter the signal received from the second electromagnetic field transceiver (e.g., using the amplification circuit 204, data acquisition card 206, and filtering process block 208 of FIG. 2) to produce a first modified signal.

At step 714, the processor device may amplify, digitize, and filter the signal received from the third electromagnetic field transceiver (e.g., using the amplification circuit 204, data acquisition card 206, and filtering process block 208 of FIG. 2) to produce a second modified signal.

At step 716, the signal processing circuit may determine a position and motion trajectory of the first electromagnetic field transceiver (e.g., relative to a defined origin point) based on the first and second modified signals. For example, a LUT stored in a memory device (e.g., memory device 418 of FIG. 4) may be accessed by the processor device, and the voltages of the first and second modified signals may be compared to the LUT in order to determine two sets of coordinates defining the position of the first electromagnetic field transceiver with respect to the second and third electromagnetic field transceivers. In some embodiments, the coordinate with the lowest RMSE may be selected as corresponding to the position of the first electromagnetic field transceiver. The selected coordinate may then be modified to correspond to the position of the first electromagnetic field transceiver relative to a defined origin point. The modified coordinate may, in some embodiments, be stored in the memory device coupled to the processor device, which may enable a motion trajectory to be derived from multiple stored, modified coordinates (e.g., positions) of the first electromagnetic field transceiver collected over time.

It should be understood that the method of FIG. 7 may be performed periodically in order to collect and store multiple determined positions of the first electromagnetic field transceiver over time so that a motion trajectory may be calculated for the first electromagnetic field transceiver.

Figure 8A:
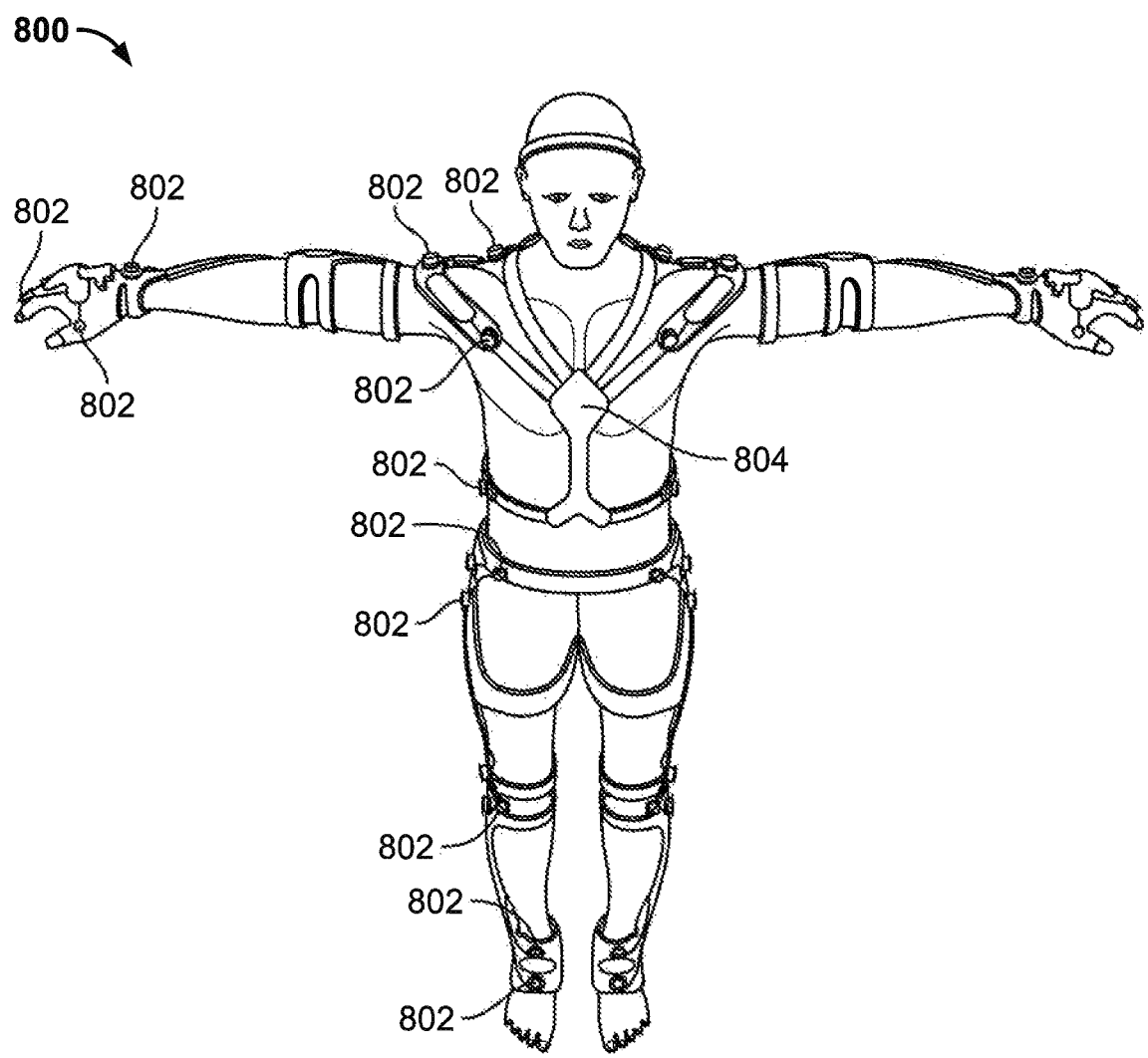
FIG. 8A is a front-perspective view of an illustrative system for obtaining and tracking human posture in accordance with an embodiment of the present invention.
Figure 8B:
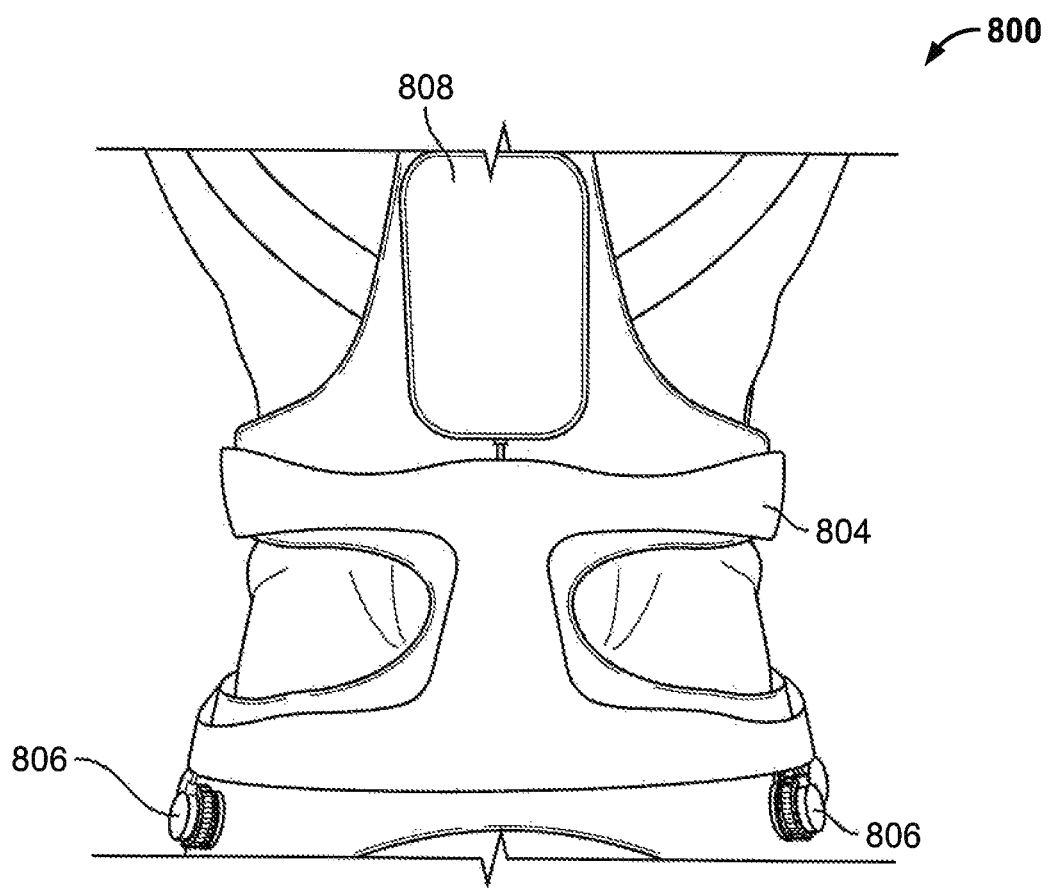
FIG. 8B is a rear view of an illustrative system for obtaining and tracking human posture in accordance with an embodiment of the present invention.

FIGS. 8A and 8B show an illustrative embodiment of a system 800 for obtaining and tracking human posture. As shown, the system 800 includes a harness 804 worn by a subject. The harness 804 may extend across the torso, arms, legs, head, hands, and feet of the subject, and may include many electromagnetic field transceivers 802 and 806. For example, the electromagnetic field transceivers 806 may be of the first type and the electromagnetic field transceivers 802 may be of the second type (as described previously). A processor device 808 (e.g., the processor device 410 of FIG. 4) may also be attached to the harness 804. Cables configured to convey signals (e.g., electrical signals or fiber optic signals) may be embedded within or otherwise attached to the harness 804 and may couple the processor device 808 to the electromagnetic field transceivers 802 and 806.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method of obtaining a human posture, comprising:
   receiving, by a first electromagnetic field transceiver disposed on a limb of a subject from a processor device, a waveform generated by a transmit waveform generating circuit of the processor device;

transmitting, via an inductive coil of the first electromagnetic field transceiver, a low frequency signal and, via an antenna of the first electromagnetic field transceiver, a high frequency signal, the low frequency signal having a frequency that is less than a frequency of the high frequency signal, wherein before transmission, the low frequency signal and the high frequency signal form first and second near field distributions combining into a near quasi-stationary electromagnetic field distribution;

receiving, via an antenna of a second electromagnetic field transceiver, the signal;

sending, by the second electromagnetic field transceiver, the received signal to the processor device;

determining, with the processor device, a voltage of the received signal based upon the near quasi-stationary electromagnetic field distribution; and determining, with the processor device, a coordinate corresponding to a position of the first electromagnetic field transceiver relative to a position of the second electromagnetic field transceiver based at least on the determined voltage.

2. The method of claim 1, further comprising:
amplifying, with an amplification circuit of the processor device, the received signal.

3. The method of claim 2, further comprising:
sending, by the amplification circuit, the received signal to a data acquisition card of the processor device; and
digitizing, with an analog-to-digital convertor of the data acquisition card, the received signal.

4. The method of claim 3, further comprising:
sending, by the data acquisition card, the received signal to a filtering process block of the processor device; and
filtering, with the filtering process block, the received signal.

5. The method of claim 4, further comprising:
sending, by the filtering process block, the received signal to a signal processing circuit of the processor device, wherein the signal processing circuit performs the steps of determining the voltage of the received signal and determining the coordinate corresponding to the position of the first electromagnetic field transceiver relative to the position of the second electromagnetic field transceiver based at least on the determined voltage.

6. The method of claim 1, wherein determining the coordinate corresponding to the position of the first electromagnetic field transceiver relative to the position of the second electromagnetic field transceiver based at least on the determined voltage comprises:
accessing, with the processor device, a look-up table stored in a memory device coupled to the processor device, the look-up table relating voltages of received signals to distance and angle pairs; and
comparing, with the processor device, the determined voltage to the look-up table to determine a distance between the first electromagnetic field transceiver and the second electromagnetic field transceiver and an angle between the first electromagnetic field transceiver and the second electromagnetic field transceiver.

7. The method of claim 1, wherein the second electromagnetic field transceiver is disposed on a torso of the subject.

8. The method of claim 1, wherein the antenna of the second electromagnetic field transceiver is a low frequency antenna that comprises a coil coupled in parallel with a capacitor.

9. The method of claim 1, further comprising:
with a signal switching matrix of the processor device, selecting the first electromagnetic field transceiver for transmission of the signal; and
with the signal switching matrix of the processor device, selecting the second electromagnetic field transceiver for reception of the signal.

10. The method of claim 1, further comprising:
storing, with the processor device, the coordinate at a memory device coupled to the processor device;
generating, with the processor device, a motion trajectory of the first electromagnetic field transceiver over time based on a plurality of coordinates of the first electromagnetic field transceiver stored at the memory device; and
storing, at the memory device, the generated motion trajectory.

11. The method of claim 10, further comprising:
sending, from the memory device, the generated motion trajectory to an electronic device; and
depicting, as part of a user interface shown on a display of the electronic device, a computer generated model of a human that is animated based at least on the generated motion trajectory.

12. A system comprising:
a first transceiver disposed on an extremity of a subject and comprising a first antenna;
a second transceiver disposed on a torso of the subject and comprising a second antenna; and
a processor device coupled to the first and second transceivers via cables, the processor device comprising:
a signal processing circuit;
a signal source coupled to the signal processing circuit, the signal source being configured to generate a waveform; and
a signal switching matrix coupled to the signal processing circuit, the signal source, the first transceiver, and the second transceiver, the switching matrix being configured to route the waveform to the first transceiver, the first transceiver being configured to transmit a signal corresponding to the waveform via the first antenna, the second transceiver being configured to receive the signal as a first received signal via the second antenna and to send the first received signal to the switching matrix, the switching matrix being configured to route the first received signal to the signal processing circuit, and the signal processing circuit being configured to determine a distance and an angle between the first transceiver and the second transceiver based only on a first voltage of the first received signal.

13. The system of claim 12, further comprising: a third transceiver disposed on the torso of the subject and comprising a third antenna, the third transceiver being configured to receive the signal as a second received signal via the third antenna and to send the second received signal to the switching matrix, the switching matrix being configured to route the second received signal to the signal processing circuit, and the signal processing circuit being configured to determine the distance and the angle between the first transceiver and the second transceiver based further on a second voltage of the second received signal.

14. The system of claim 13, further comprising: a memory coupled to the signal processing circuit, the memory being configured to store a look-up table that relates voltages of signals received by the second and third transceivers from the first transceiver to coordinates, the signal processing circuit being configured to compare the first voltage and the second voltage to the look-up table to identify first and second coordinates, the signal processing circuit being configured to identify which of the first and second coordinates has a lowest root-mean square error, the identified coordinate of the first and second coordinates corresponding to the distance and the angle between the first transceiver and the second transceiver, and the memory being configured to store the identified coordinate.

15. The system of claim 14, the memory being configured to store a plurality of coordinates corresponding to positions of the first transceiver over time, the signal processing circuit being configured to generate a motion trajectory of the first transceiver based on the plurality of coordinates, and the memory being configured to store the motion trajectory.

16. The system of claim 12, the first transceiver comprising:
a port coupled to a first cable of the cables, the port configured to receive the waveform;
a ground terminal;
a coil having an inductance and being coupled between the port and the ground terminal; and
a capacitance coupled in parallel with the coil between the port and the ground terminal, the coil and the capacitance forming the first antenna.

17. The system of claim 16, the first transceiver further comprising:
a printed circuit antenna coupled to the port and configured to operate in a 2.4 GHz frequency band.

18. The system of claim 12, wherein the processor device further comprises:
an amplifier configured to amplify the first received signal;
a digital acquisition card configured to digitize the first received signal; and
a filtering process block configured to perform digital filtering of the first received signal.

19. The system of claim 12, further comprising:
a wearable harness that comprises the processor device, the cables, the first transceiver, and the second transceiver.

* * * * *